US010449353B2

(12) United States Patent
Shoberg et al.

(10) Patent No.: US 10,449,353 B2
(45) Date of Patent: Oct. 22, 2019

(54) ELECTRODE ASSEMBLIES, METHODS, AND COMPONENTS THEREOF FOR IMPLANTABLE MEDICAL ELECTRICAL LEADS

(71) Applicant: Medtronic, Inc., Minneapolis, MN (US)

(72) Inventors: Bret R. Shoberg, Hanover, MN (US); Gregory A. Boser, Richfield, MN (US); Michael T. Hegland, Mounds View, MN (US); Robert L. Olson, White Bear Lake, MN (US); Dale F. Seeley, Spring Park, MN (US); Jacob W. Silverberg, Blaine, MN (US); Suraj Rama, South Amboy, NJ (US)

(73) Assignee: MEDTRONIC, INC., Minneapolis, MN (US)

( * ) Notice: Subject to any disclaimer, the term of this patent is extended or adjusted under 35 U.S.C. 154(b) by 104 days.

(21) Appl. No.: 15/493,932

(22) Filed: Apr. 21, 2017

(65) Prior Publication Data
US 2017/0312500 A1    Nov. 2, 2017

Related U.S. Application Data

(60) Provisional application No. 62/328,736, filed on Apr. 28, 2016.

(51) Int. Cl.
*A61N 1/05*       (2006.01)
*A61N 1/36*       (2006.01)
(Continued)

(52) U.S. Cl.
CPC ............. *A61N 1/0551* (2013.01); *A61N 1/05* (2013.01); *A61N 1/3605* (2013.01); *H01R 24/58* (2013.01);
(Continued)

(58) Field of Classification Search
CPC ...... A61N 1/0551; A61N 1/05; A61N 1/3605; H01R 24/58; H01R 2107/00; H01R 2201/12
See application file for complete search history.

(56) References Cited

U.S. PATENT DOCUMENTS 5,935,159 A    8/1999   Cross, Jr. et al.
7,130,700 B2   10/2006  Gardeski et al.
(Continued)

FOREIGN PATENT DOCUMENTS

EP    0041791 A1    12/1981
EP    2789336 A1    10/2014
WO    2012038378 A1    3/2012

OTHER PUBLICATIONS

International Search Report and Written Opinion, PCT/US2017/029112, dated Nov. 4, 2017.

*Primary Examiner* — Lindsey G Wehrheim
(74) *Attorney, Agent, or Firm* — Withers & Keys, LLC

(57) ABSTRACT

An implantable medical electrical lead includes an electrode assembly in which an electrical junction between a first conductor and an inner surface of a first electrode of the assembly is wedged within a first channel of at least one core member of the assembly, around which the first electrode extends. The at least one core member is formed from an insulating material, and the first channel may be one of a plurality of longitudinally extending channels arrayed around a circumference of a central lumen of the assembly, which is defined by the at least one core member. The first conductor extends along a length of the assembly, for example, defined between the first electrode and a second electrode thereof, in a helical path that travels around the central lumen.

36 Claims, 9 Drawing Sheets

(51) Int. Cl.
*H01R 24/58* (2011.01)
*H01R 107/00* (2006.01)
(52) U.S. Cl.
CPC ...... *H01R 2107/00* (2013.01); *H01R 2201/12* (2013.01)

(56) References Cited

U.S. PATENT DOCUMENTS

| | | |
|---|---|---|
| 7,184,838 B2 | 2/2007 | Cross, Jr. |
| 8,055,354 B2 | 11/2011 | Zarembo et al. |
| 8,567,055 B2 | 10/2013 | Fan et al. |
| 8,968,331 B1 | 3/2015 | Sochor |
| 2004/0097965 A1* | 5/2004 | Gardeski ........... A61M 25/0021 606/129 |
| 2006/0089691 A1 | 4/2006 | Kaplan et al. |
| 2013/0325086 A1 | 5/2013 | Sommer et al. |
| 2015/0165217 A1 | 6/2015 | Hughes |

* cited by examiner

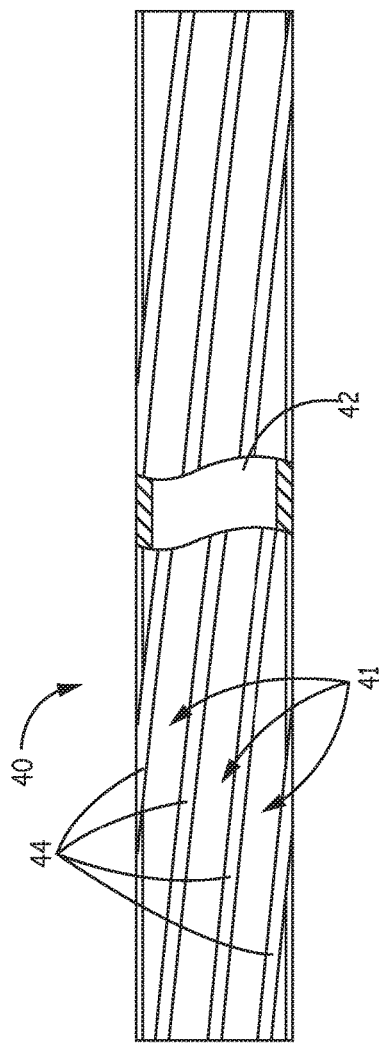
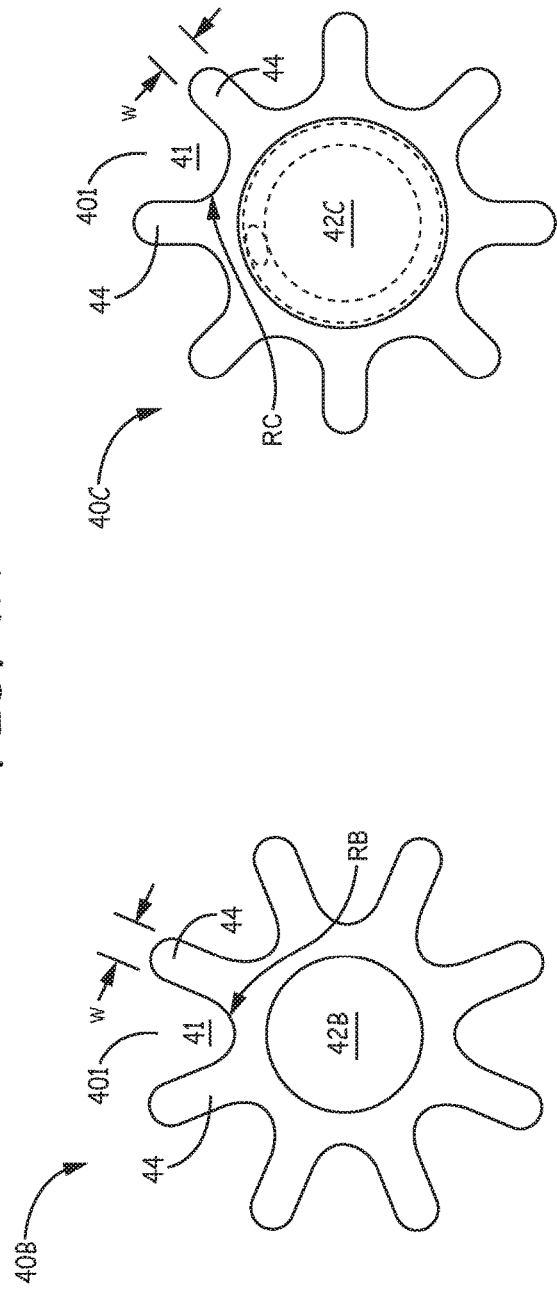
FIG. 4A
FIG. 4B
FIG. 4C

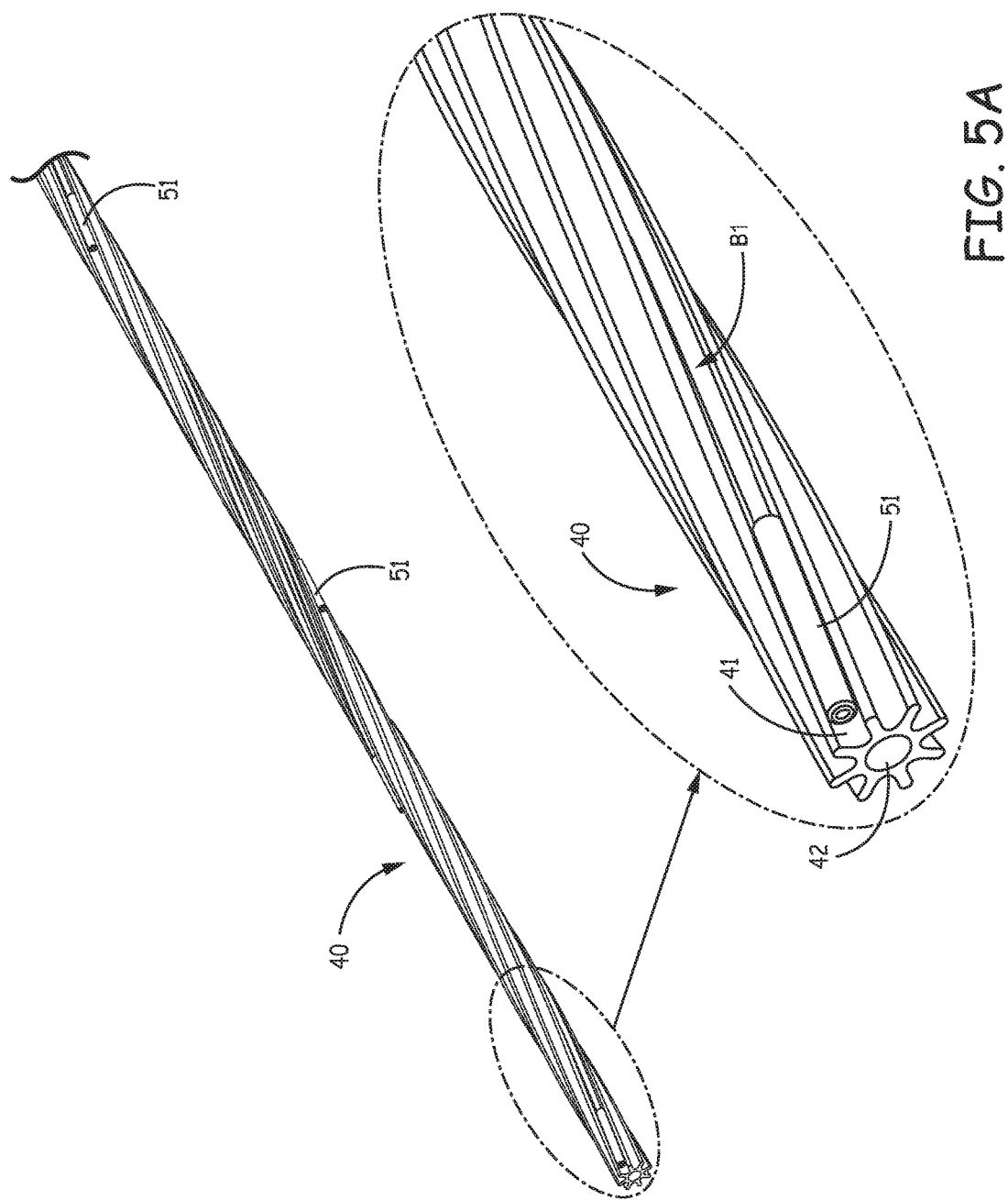

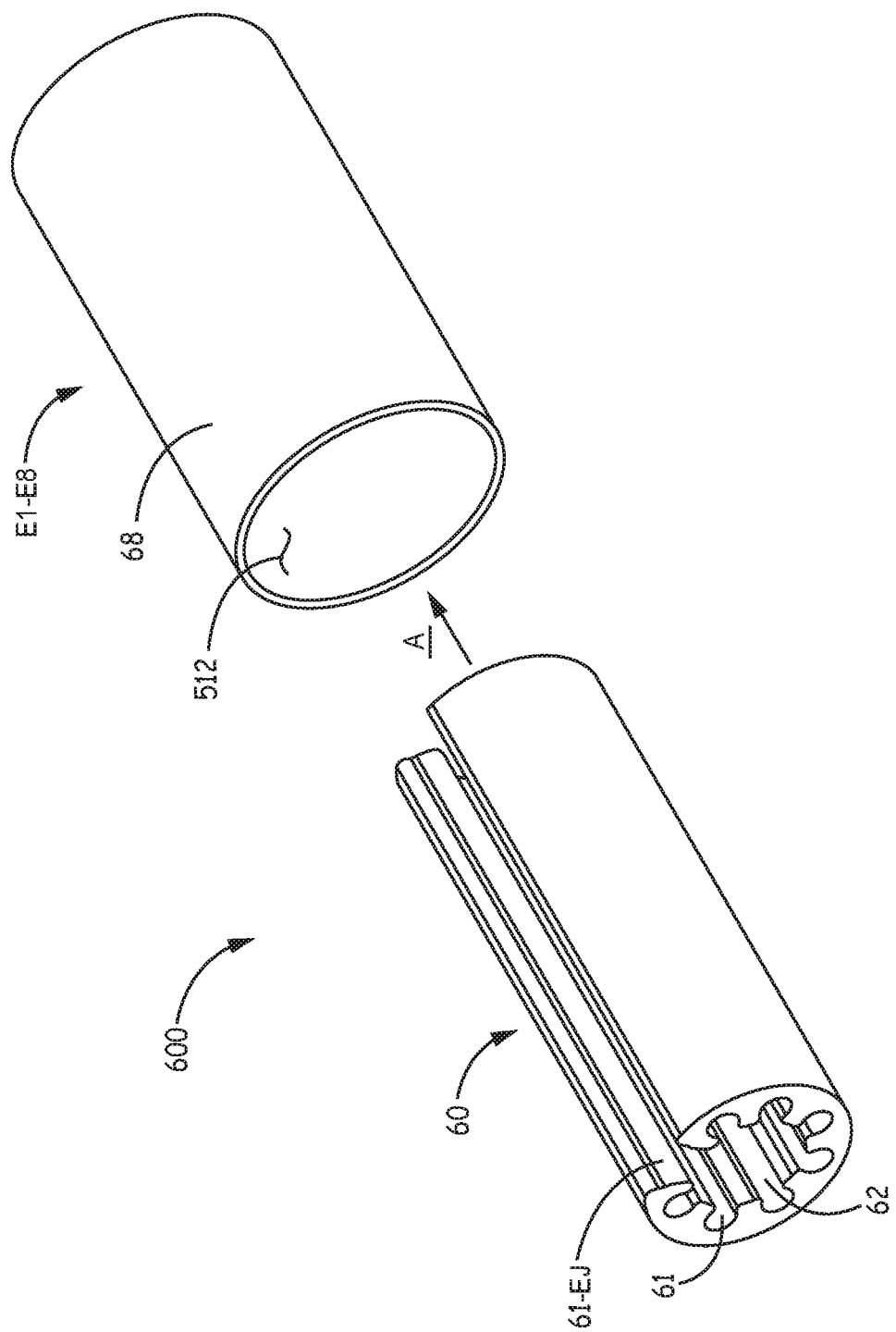

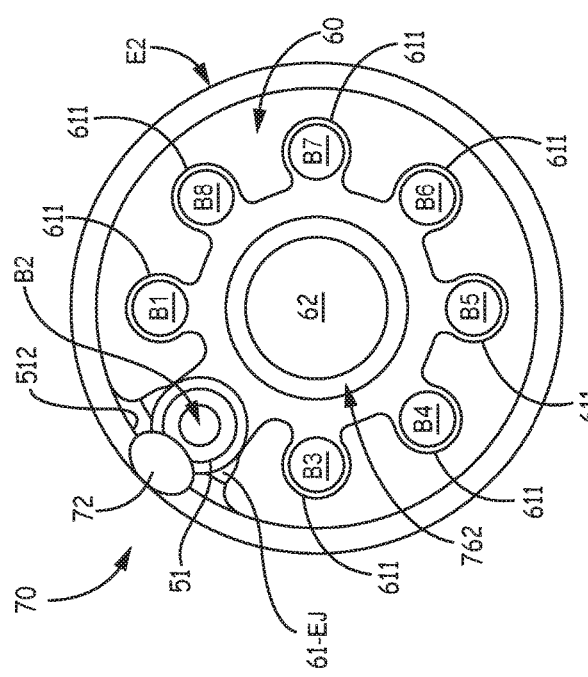
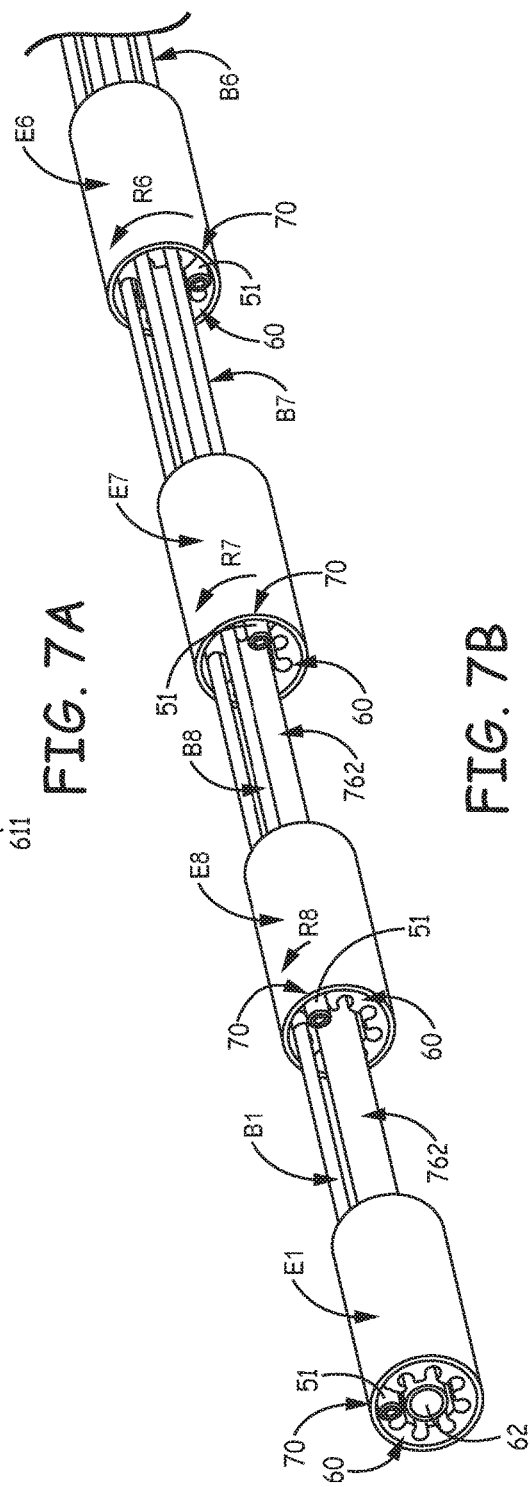
FIG. 7A
FIG. 7B

ELECTRODE ASSEMBLIES, METHODS, AND COMPONENTS THEREOF FOR IMPLANTABLE MEDICAL ELECTRICAL LEADS

RELATED APPLICATIONS

This application claims the benefit of the filing date of U.S. Provisional Application Ser. No. 62/328,736, filed Apr. 28, 2016, entitled "ELECTRODE ASSEMBLIES, METHODS, AND COMPONENTS THEREOF FOR IMPLANTABLE MEDICAL ELECTRICAL LEADS", which is incorporated herein in its entirety.

TECHNICAL FIELD

The present disclosure is related to implantable medical electrical leads, and more particularly to electrode assemblies thereof, and to related components and methods of manufacture.

BACKGROUND

Implantable medical devices are commonly used today to treat conditions such as cardiac arrhythmias, pain, incontinence, sleep disorders, and movement disorders such as Parkinson's disease and epilepsy. One known type of implantable medical device, a neurostimulator, delivers mild electrical impulses to neural tissue through an array of electrodes. Typically, such devices are part of totally implantable stimulation systems and may be controlled by a physician or a patient through the use of an external programmer connected to the device, for example, via telemetry. This type of device generally includes a power source and a pulse generator contained in a hermetically sealed enclosure. Such a system may also include a lead extension, and a stimulation lead, of which the aforementioned array of electrodes is an integral part. An electrode assembly of the lead may be located in proximity to a distal end thereof, and include from four to eight electrodes arranged in the array. A proximal end of the lead may connect to the extension, which electrically couples the lead to the pulse generator of the device, for example, by being plugged into a connector module of the device.

FIG. 1 is a schematic showing an example of a stimulation system, like that described above, implanted in a patient 28 for spinal cord stimulation. FIG. 1 illustrates a device 20 of the system being implanted in an abdominal region of patient 28, and a lead 24 of the system extending along a spinal cord 30, and being electrically coupled to device 20 via an extension 22, which is shown connected to lead 24 by a connector 32. FIG. 1 further illustrates lead 24 including an electrode array 26 positioned along spinal cord 30, for example, having been percutaneously introduced through a needle and into an epidural space that surrounds spinal cord 30. Although a variety of known electrode assemblies are suitable for arrays like electrode array 26, there is still a need for new assemblies.

SUMMARY

In an electrode assembly for an implantable medical electrical lead, according to some embodiments disclosed herein, an electrode junction between a first conductor, of a plurality of conductors of the assembly, and an inner surface of a first electrode, or a plurality of electrodes of the assembly, is wedged within a first channel of a plurality of longitudinally extending channels of at least one core member of the assembly, around which the first electrode extends. The junction, in some embodiments, may be formed by a conductive sleeve swaged around a distal end of the first conductor, and a weld joint formed between the inner surface of the first electrode and the swaged conductive sleeve. The at least one core member, for example, being formed from an insulating material, defines a central longitudinally extending lumen of the assembly, and the plurality of longitudinally extending channels are arrayed around a circumference of the central lumen, with each channel having an opening that extends along an entire length thereof. In some embodiments, the opening of each channel faces outward, away from the central lumen. The first conductor extends along a helical path that travels around the central lumen of the assembly and from a proximal end of the length of the assembly to a distal end of a length of the assembly, wherein the distal end may be defined by the first electrode and the proximal end by a second electrode of the plurality of electrodes. The second electrical junction, formed between an inner surface of the second electrode and a second conductor of the plurality of conductors may be wedged within a second channel of the plurality of channels of the at least one core member.

According to some embodiments, the at least one core member is a single flexible core member that extends along the length of the assembly, and each channel of the plurality of channels of the single core member extends along a corresponding helical path that travels around the central lumen. According to some alternate embodiments, the at least one core member includes a plurality of core members spaced apart from one another along the length of the assembly, wherein each core member has a corresponding electrode of the plurality of electrodes extending thereabout. In these alternate embodiments, a first core member of the plurality of core members includes the aforementioned first channel in which the electrical junction between the first conductor and the inner surface of the first electrode is wedged, while a second core member of the plurality includes the aforementioned second channel in which the electrical junction between the second conductor and the inner surface of the second electrode is wedged. According to some of the embodiments that include the plurality of core members, the opening of each channel of the plurality of channels of each core member faces inward toward the central lumen, and the assembly may further include an elongate tubular sidewall extending along the length of the assembly to isolate the channels of the plurality of core members from the central lumen.

According to some embodiments of an implantable medical electrical lead, which includes any of the above-described electrode assembly embodiments, a distal-most tip of the lead, for example, located in close proximity to the distal end of the length of the electrode assembly, is integrally molded together with each spacer from an insulative material, wherein each spacer is located between adjacent electrodes of the plurality of electrodes.

A method for manufacturing any of the above-described electrode assembly embodiments may include the following steps: wedging a conductive distal end of the first conductor in one of the plurality of channels within the first electrode so that the conductive distal end of the first conductor makes intimate contact with the inner surface of the first electrode; placing the first conductor in the one, or another channel within the second electrode; wedging a conductive distal end of a second conductor in yet another channel within the second electrode so that the conductive distal end of the second conductor makes intimate contact with an inner surface of the second electrode; electrically coupling the wedged conductive distal ends of the first and second conductors to the inner surface of the first and second electrodes, respectively; and injecting an insulative material between adjacent electrodes of the plurality of electrodes. According to some methods, a single core, which includes aforementioned channels, is formed from an insulative material and inserted within each electrode of the plurality of electrodes; while, according to some alternative methods, a plurality of cores, which include the aforementioned channels, are formed from an insulative material and each core is inserted into a corresponding electrode, after which, the first and second electrodes are clocked.

An electrode component for an electrode assembly of an implantable medical electrical lead, according to some embodiments disclosed herein, includes a core formed from an insulating material and defining a central longitudinally extending lumen of the component, wherein the core includes a plurality of longitudinally extending channels arrayed around the central lumen, each channel being sized to receive an elongate conductor therein, and each channel having an opening extending along an entire length thereof, each opening facing toward the central lumen. The component further includes a longitudinally extending conductive layer overlaying the core, wherein a single channel of the plurality of channels of the core has another, second opening extending along the entire length thereof, the other opening facing toward an inner surface of the conductive layer.

BRIEF DESCRIPTION OF THE DRAWINGS

The following drawings are illustrative of particular embodiments and do not limit the scope of the disclosure. The drawings are not to scale (unless so stated) and are intended for use in conjunction with the explanations in the following detailed description. Embodiments will hereinafter be described in conjunction with the appended drawings wherein like numerals/letters denote like elements, and:

FIG. 4A is a plan view of a core member for an electrode assembly, for example, like the electrode assembly of FIG. 3, according to some embodiments;

FIGS. 4B-C are plan views of alternative profiles for the core member of FIG. 4A, according to some embodiments;

FIG. 5A is a perspective view of a portion of a subassembly for an electrode assembly, according to some embodiments;

FIG. 6A is an exploded perspective view of an electrode component, for an electrode assembly, according to some alternate embodiments;

FIG. 7A is an end view including a schematic representation of an electrical junction in an electrode assembly that includes the component of FIGS. 6A-B, according to some embodiments; and FIG. 7B is a perspective view of a portion of the electrode assembly that includes a plurality of the components of FIGS. 6A-B, according to some embodiments.

DETAILED DESCRIPTION

The following detailed description is exemplary in nature and is not intended to limit the scope, applicability, or configuration of inventive embodiments disclosed herein in any way. Rather, the following description provides practical examples, and those skilled in the art will recognize that some of the examples may have suitable alternatives. Examples of constructions, materials, dimensions and fabrication processes are provided for select elements and all other elements employ that which is known by those skilled in the art.

Figure 1:
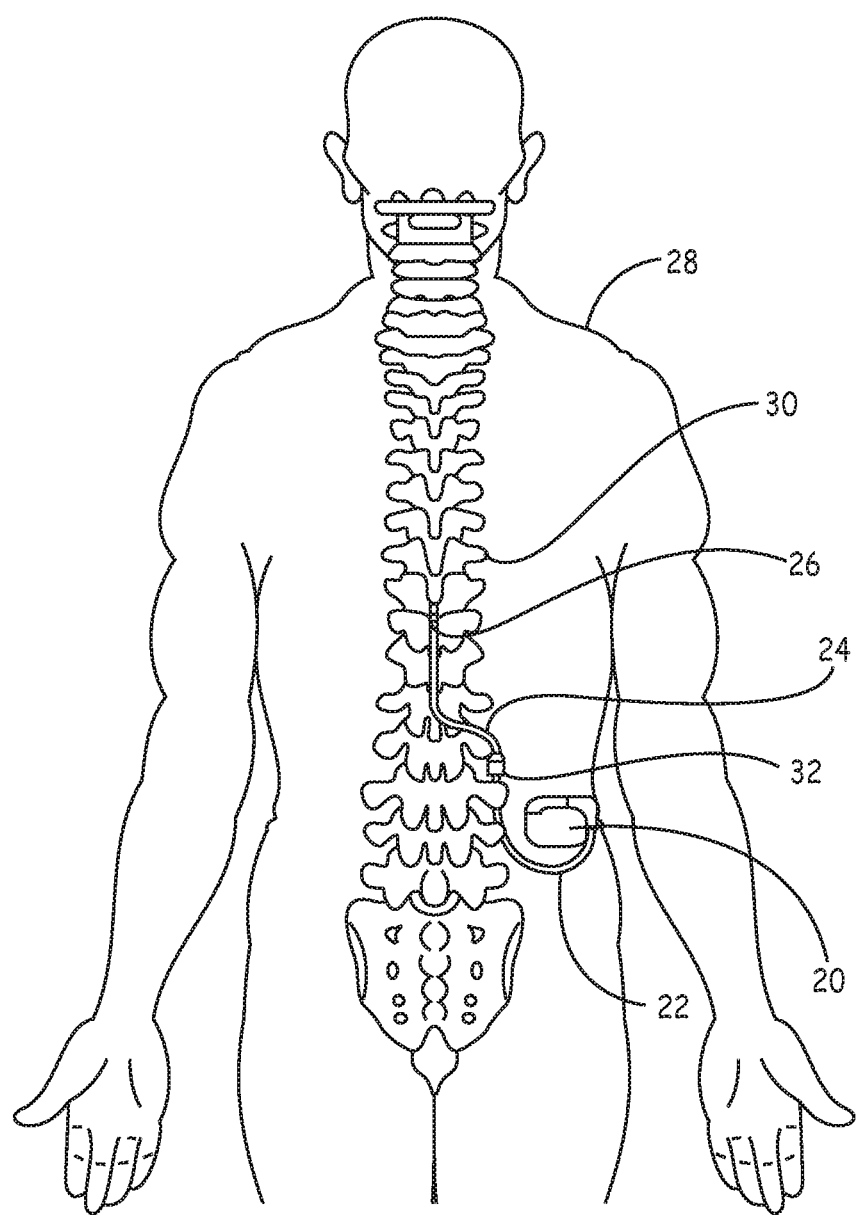
FIG. 1 is a schematic showing an exemplary stimulation system implanted in a patient.
Figure 2A:
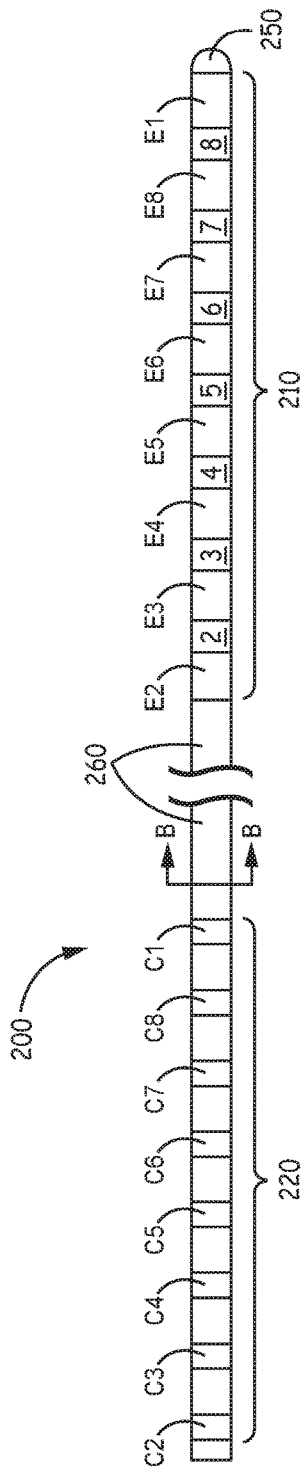
FIG. 2A is a plan view of an exemplary implantable medical electrical lead, according to some embodiments, which may be employed by the system of FIG. 1.

FIG. 2A is a plan view of an exemplary implantable medical electrical lead 200, according to some embodiments, which may be employed by the system of FIG. 1 in lieu of lead 24. FIG. 2A illustrates lead 200 including a connector 220, an electrode assembly 210, an insulative body 260 extending therebetween, and a distal-most tip 250. FIG. 2A further illustrates electrode assembly 210 including a plurality of electrodes E1-E8 spaced apart from one another along a length of assembly 210, wherein a distal end of the length of assembly 210 is defined by a first electrode E1 of the plurality, and a proximal end of the length of assembly 210 is defined by a second electrode E2 of the plurality. In an exemplary embodiment, each electrode E1-E8 may be formed from a 90/10 or 80/20 Platinum Iridium alloy, and a length of each electrode E1-E8 may be in a range from approximately 0.06 inch to approximately 0.118 inch. With further reference to FIG. 2A, electrode assembly 210 further includes a plurality of insulative spacers 2-8, each of which is shown interposed between pairs of adjacent electrodes, wherein spacers 2-8 are preferably approximately isodiametric with electrodes E1-E8. In some embodiments, distal-most tip 250 and spacers 2-8 may be integrally formed together from an insulative material, such as medical grade polyurethane or silicone rubber, for example, by a molding process. In an exemplary embodiment an outer diameter of assembly 210 is approximately 0.05 inch, and a length of distal-most tip 250 may be about 0.020 inch.

Figure 2B:
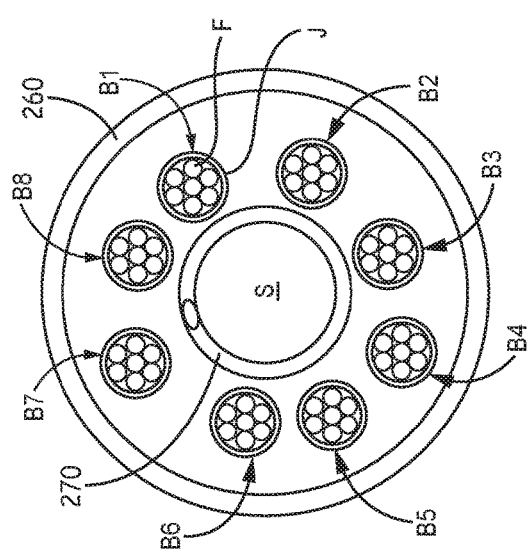
FIG. 2B is a cross-section view through section line B-B of FIG. 2A.

According to the illustrated embodiment, each electrode E1-E8 is electrically coupled to a corresponding contact C1-C8 of connector 220 by a corresponding conductor that extends within insulative body 260, for example, a corresponding conductor of a plurality of conductors B1-B8 shown in the cross-section view of FIG. 2B. (It should be noted that connector 220 also includes insulative spacers interposed between adjacent pairs of contacts.) Each conductor B1-B8 is preferably formed from a plurality of conductive filars F bundled together in a cable configuration according to any suitable arrangement known to those skilled in the art; and each cable preferably includes an insulative jacket J extending thereabout and along a length thereof. According to an exemplary embodiment, each conductor B1-B8 has an outer diameter of approximately 0.006 inch, wherein the cable of each includes seven filars F formed from the MP35N alloy known to those skilled in the art, and wherein jacket J of each is formed by an overextruded layer of a medical grade fluoropolymer (e.g., ethylene tetrafluoroethylene), which may be approximately 0.0008 inch thick. In some alternate embodiments, each conductor B1-B8 may include a single wire, for example, having a diameter of about 0.004 inch, in lieu of filars F.

With further reference to FIG. 2B, a coil 270 also extends within body 260, for example, to define at least a portion of a longitudinally extending stylet lumen S, which may extend from a proximal opening thereof (located in proximity to contact C2), and through connector 220, lead body 260 and electrode assembly 210. According to an exemplary embodiment, coil 270 is formed from MP35N alloy with a wire diameter of about 0.0025 inch, has an outer diameter of approximately 0.018 inch, and an inner diameter of approximately 0.013 inch to accommodate passage therethrough of a stylet that may be useful for advancing lead 200 into the aforementioned epidural space to position electrodes E1-E8 at a desired stimulation site along spinal cord 30 (FIG. 1). FIG. 2B illustrates insulative body 260 of lead 200 having a tubular sidewall that extends around conductors B1-B8 and coil 270. Although not shown, the tubular sidewall of body 260 may have a multi-lumen configuration, for example, to hold coil 270 and each of conductors B1-B8, or groups thereof, in individual lumens. In any case, body 260 may be formed from an insulative material, such as a medical grade polyurethane or silicone rubber, or a combination thereof, and may further include an embedded reinforcing material and/or an overlay material, according to any suitable design configuration known to those skilled in the art.

Figure 3:
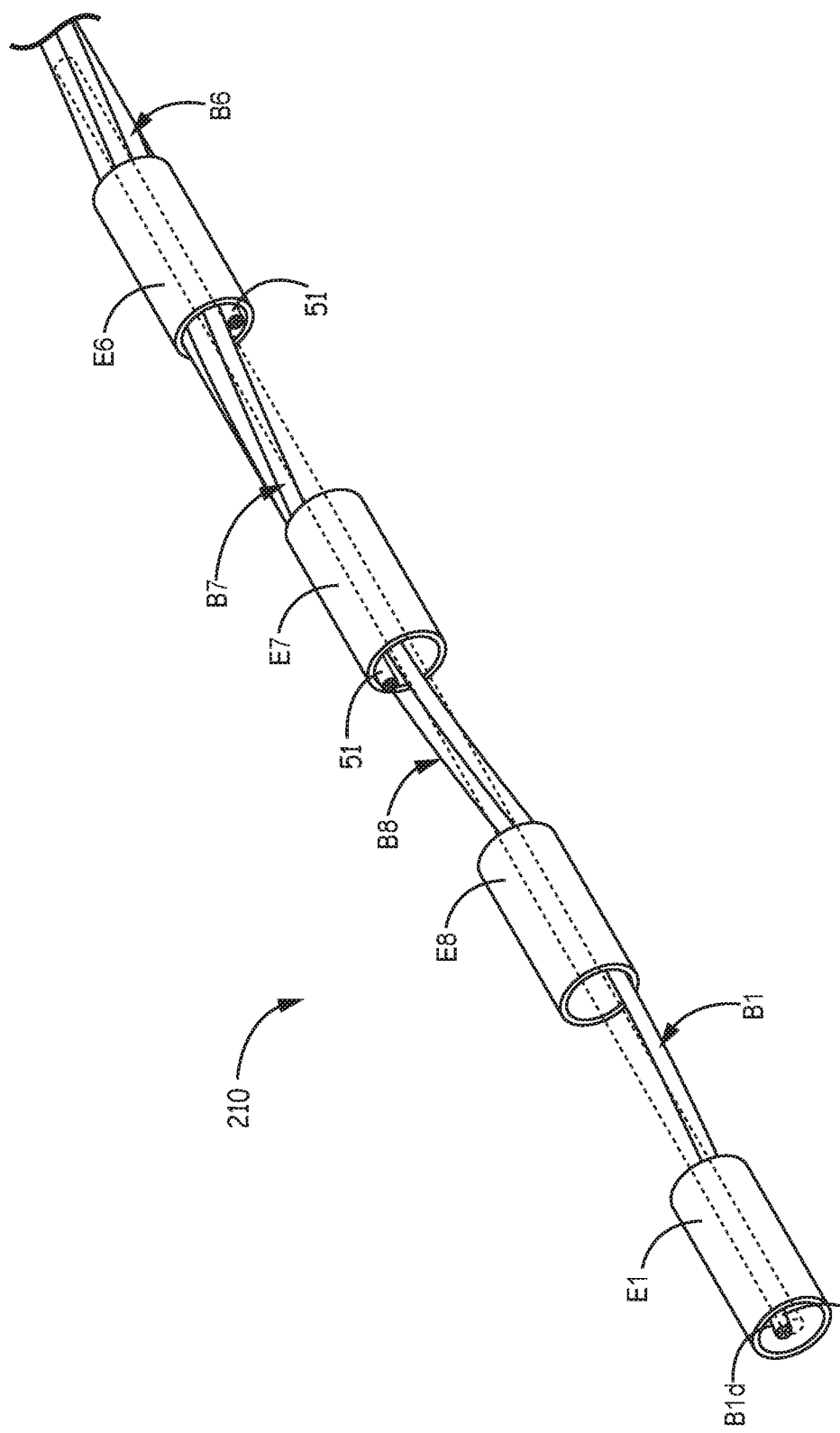
FIG. 3 is a perspective view of a portion of an electrode assembly, according to some embodiments, which may be employed by the lead of FIG. 2A.

FIG. 3 is a perspective view of a portion of electrode assembly 210, according to some embodiments, wherein conductors B1, B8, B7, B6 are shown extending along helical paths that can provide strain relief for the conductors along the length of assembly 210. The helical path of first conductor B1 extends from a distal end B1d thereof, at first electrode E1, to the proximal end of assembly 210, which is defined by second electrode E2 (FIG. 2A), and travels around a longitudinally extending central lumen of assembly 210 (shown by a dashed line in FIG. 3), for example, to provide strain relief for the conductors. According to an exemplary embodiment, the helical path of first conductor B1 extends around the central lumen in a pitch of approximately 360 degrees for every inch of length. Likewise the helical path of each of conductors B3-B8 extends proximally from the corresponding electrode E3-E8 to the proximal end of assembly 210 with a similar pitch. The length of electrode assembly 210 may range from one inch to three inches, preferably being about two inches. Although assembly 210 is shown including eight electrodes, it should be noted that a greater or fewer number of electrodes may be incorporated in assemblies that are within the scope of the present disclosure.

According to embodiments of the present disclosure, at least one core member formed from an insulating material defines the central lumen of assembly 210, and includes a plurality of longitudinally extending channels arrayed around the circumference of the central lumen. According to some embodiments, electrode assembly 210 includes a single flexible core member whose plurality of channels route conductor B1, B3-8 along their helical paths, for example, according to any of the embodiments described below in conjunction with FIGS. 4A-5B. According to some alternate embodiments, electrode assembly 210 includes a plurality of core members, one corresponding to each electrode E1-E8, for example, according to any of the embodiments described below in conjunction with FIGS. 6A-7B. The employment of at least one core member, according to any of the embodiments described below, provides a number of enhancements over prior art electrode assemblies, for example, related to ease of assembly, strain relief, stylet passage and steering of electrodes for positioning at the desired stimulation site, and electrical isolation between conductors.

Figure 5B:
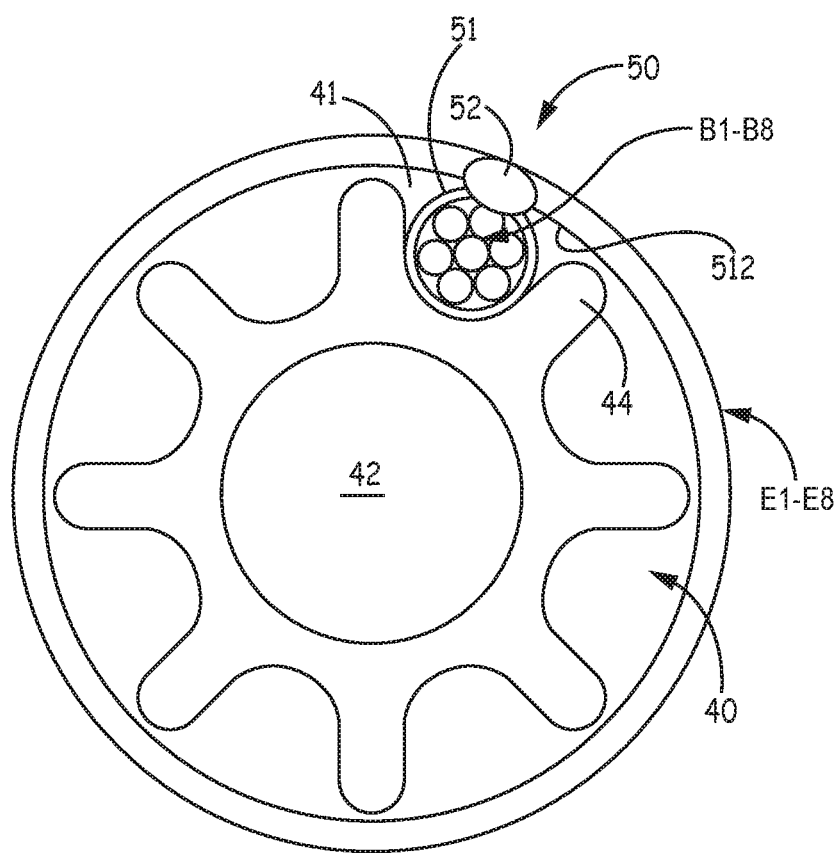
FIG. 5B is a schematic end view of an electrical junction in an electrode assembly, according to some embodiments.

FIG. 4A is a plan view of a core member 40 for assembly 210, according to some embodiments. FIG. 4A illustrates core member 40 including a plurality of longitudinally extending channels 41, each being defined by adjacent ridges 44 and extending along a helical path that travels around a central lumen 42 of core member 40. As alluded to above, certain embodiments of electrode assembly 210 include core member 40, such that lumen 42 corresponds to the central lumen of assembly 210, and each of conductors B1, B3-B8 is routed along the corresponding helical path by being positioned in the corresponding channel 41 of core member 40, for example, as illustrated in FIG. 5A. As alluded to above, the helical path for each of conductors B1, B3-B8 provides strain relief, for example, to reduce stress on the conductors, if electrode assembly 210 is implanted along a curved path and/or undergoes cyclical loading/bending in the implant environment. The aforementioned pitch may be optimized to provide the necessary strain/stress relief according to the intended implant environment for assembly 210, and, in some cases, channels 41 may not extend in a helical path. In some embodiments, lumen 42 may have a lubricious surface, for example, being lined with a medical grade polyimide or any other suitable 'slippery' polymer known in the art. In addition to routing conductors B1, B3-B8, each channel 41 of core member 40 serves to hold an electrical junction for each conductor B1-B8, for example, as described below in conjunction with FIGS. 5A-B.

FIGS. 4B-C are plan views of alternative profiles 40B, 40C for core member 40, according to some embodiments, wherein FIG. 4B shows profile 40B defining a central lumen 42B of a relatively smaller size than a central lumen 42C defined by the alternative profile 40C of FIG. 4C. A diameter of central lumen 42B may be just large enough, for example, approximately 0.015 inch, to accommodate a stylet, for example, as an extension of lumen S defined by coil 270 (FIG. 2B), when coil 270 does not extend distally from insulative body 260 into electrode assembly 210. A diameter of central lumen 42C may be large enough to accommodate the extension of coil 270 therethrough as stylet lumen S (shown with dashed lines in FIG. 4C), for example, being about 0.020 inch. According to exemplary embodiments, a radius RB at the base of channel 41 in profile 40B is approximately 0.003 inch, while a radius RC at the base of channel 41 in profile 40C is approximately 0.004 inch. In either case, an end of each ridge 44 may have a width w of about 0.004 inch, and ends of adjacent ridges 44 may be spaced apart by about 0.012 inch to about 0.013 inch to define an outward facing longitudinally extending opening 401 of each channel 41, according to the exemplary embodiments. Core member 40 may be formed from a medical grade polymer, such as polyurethane, by an extrusion process, wherein an exemplary embodiment having profile 40B can be formed from a polyurethane having a durometer of 75D, and an exemplary embodiment having profile 40C can be formed from a polyurethane having a durometer of 55 D.

FIG. 5A is a perspective view of a subassembly for electrode assembly 210 with an enlarged detailed view of a distal portion of core member 40 that shows first conductor B1 assembled together therewith, according to some embodiments. FIG. 5A illustrates a conductive sleeve 51 secured around the aforementioned distal end B1d (FIG. 3) of first conductor B1, for example, by swaging, and wedged into channel 41 of core member 40 at a location corresponding to the ultimate position of first electrode E1 in electrode assembly 210. In some embodiments, after stripping a portion of insulative jacket J (FIG. 2B) of conductor B1 from around the cable at the distal end thereof, conductive sleeve 51 is swaged around the stripped cable, according to methods known in the art, so that an inner surface of conductive sleeve 51 is brought into intimate contact with the conductive filars F of conductor B1, and an outer surface of sleeve 51 remains relatively smooth. Likewise, conductive sleeves, similar to sleeve 51, are secured to distal ends of the other conductors B2-B8, prior to positioning each of conductors B2-B8 in the corresponding channel 41 with the corresponding secured sleeves wedged therein at locations along the length of core member 40 that correspond to the ultimate locations of the corresponding electrode E2-E8 in electrode assembly 210. Thus, after positioning each electrode E1-E8 around core member 40 and the swaged conductive sleeve 51 of the corresponding conductor B1-B8, an electrical coupling, or junction 50 may be completed between each conductor B1-B8 and an inner surface 512 of the corresponding electrode E1-E8, for example, as illustrated in FIG. 5B. According to some methods, the subassembly of conductors B1-B8 and core member 40 is inserted within the inner diameter of each electrode E1-E8, and then each electrode E1-E8 is slid into position along the length of core member 40. According to an exemplary embodiment, an outer diameter of core member 40 (defined at peak of each ridge 44) is approximately 0.040 inch, and an inner diameter defined by inner surface 512 of each electrode E1-E8 can range from approximately 0.042 inch to approximately 0.044 inch. In some embodiments, each electrode E1-E8 may include a longitudinal slit along a length thereof, which allows for some expansion of the inner diameter of each, for example, to provide more flexibility in positioning electrodes E1-E8 around core member 40 and the corresponding swaged conductive sleeve 51.

FIG. 5B is a schematic end view of electrical junction 50, according to some embodiments. FIG. 5B illustrates each electrical junction 50 completed by forming a weld joint 52 between each electrode inner surface 512 and the swaged sleeve 51 of the corresponding conductor B1-B8, which is wedged in the corresponding channel 41 of core member 40 to be held thereby in intimate contact with inner surface 512. An inner diameter of each electrode ring E1-E8 and an outer diameter of each swaged sleeve 51 can be optimized such that an outward pressure applied by core member 40 to wedged sleeves 51 holds each sleeve 51 in the intimate contact with the corresponding inner surface 512 to enable the formation of an excellent weld joint 52. Each weld joint 52 can be formed by any suitable laser welding method known to those skilled in the art, wherein the laser energy is directed onto an outer surface of each electrode E1-E8 at a location opposite that at which the corresponding swaged conductive sleeve 51 is in contact with inner surface 512. Directing the laser energy may be facilitated by positioning swaged sleeves 51 and electrodes E1-E8 relative to one another so that a portion of each sleeve 51 can be seen protruding slightly from a distal edge of the corresponding electrode E1-E8, for example, as shown in FIG. 3.

According to some methods, automated visualization can be employed to locate the protruding portion of each sleeve 51 and then position the laser source accordingly for a blind weld that penetrates through to inner surface 512 of each electrode E1-E8, to reach the corresponding conductive sleeve 51, and in some cases, through each conductive sleeve 51 as well, to reach filars F of the corresponding swaged conductor B1-B8. According to an exemplary embodiment, conductive sleeve 51 is formed from a 90/10 or 80/20 Platinum Iridium alloy, and, prior to swaging, sleeve 51 has an inner diameter of approximately 0.006 inch, an outer diameter of approximately 0.012 inch, and a length of approximately 0.06 inch. After swaging, an outer diameter of each swaged sleeve 51 may range from approximately 0.008 inch to approximately 0.010 inch.

According to some methods, when each electrode E1-E8 is properly spaced along the length of core member 40, and after each electrical junction 50 is formed, insulative spacers 2-8 (FIG. 2A) are formed. In some embodiments, as alluded to above, distal-most tip 250 of lead 200 is formed integrally with spacers 2-8, for example, by an injection molding process known to those skilled in the art, in which core member 40, with each conductors B1-B8 held in the corresponding channel 41, and positioned electrodes E1-E8, with conductors B1-B8 electrically coupled thereto, are held in a cavity of a mold while an insulative polymer material, for example, medical grade polyurethane, is injected thereabout. A length of core member 40 may extend distal to first electrode E1 to be encompassed by distal-most tip 250 in some embodiments. Furthermore, in some embodiments, core member 40 may extend into body 260 of lead 200 and support conductors B1-B8 therein.

Figure 6B:
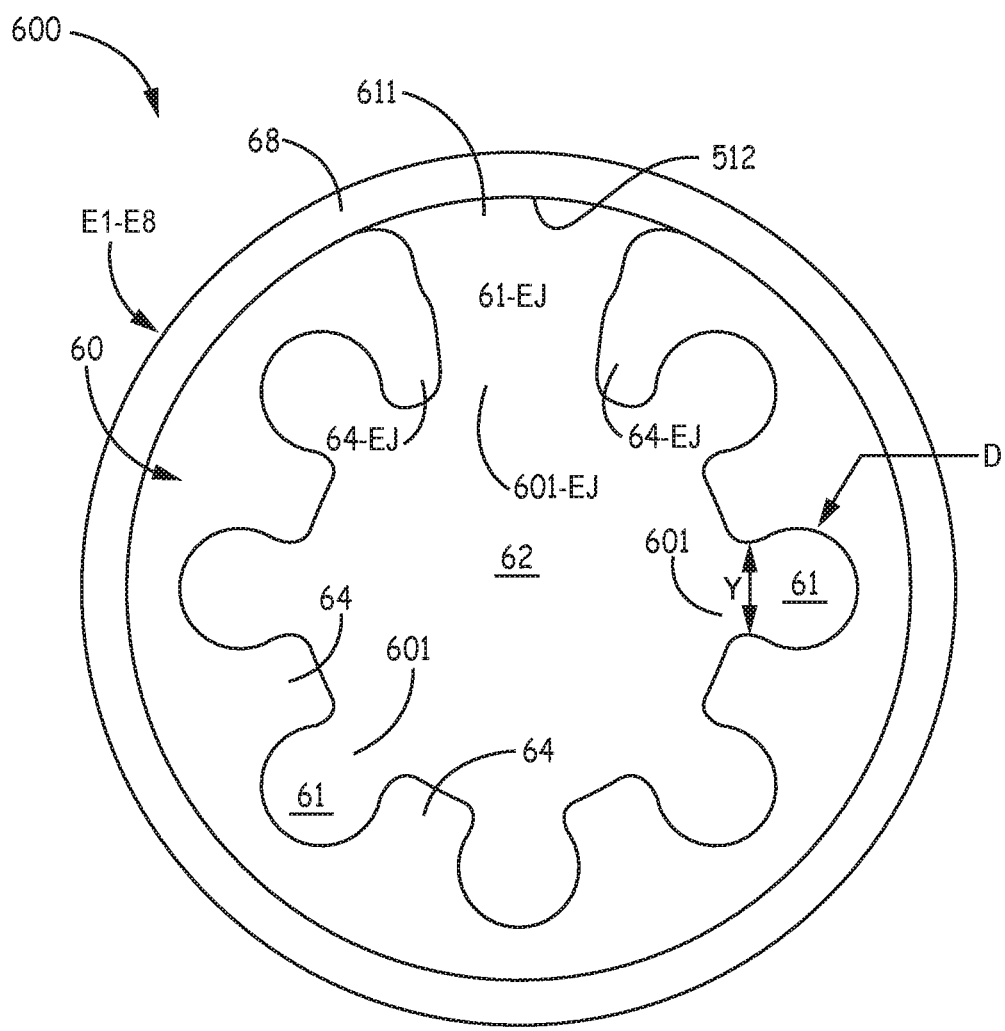
FIG. 6B is an end view of the component of FIG. 6A, according to some embodiments.

FIG. 6A is an exploded perspective view of an electrode component 600, for an electrode assembly, for example, like electrode assembly 210, according to some alternate embodiments; and FIG. 6B is an end view of component 600, wherein a longitudinally extending conductive layer 68, for example, corresponding to any of electrodes E1-E8, overlays core members 60. FIG. 6A illustrates core member 60 being configured to fit within inner surface 512 of a corresponding conductive layer 68/electrode E1-E8, for example, having been molded from a medical grade polymer material, such as polyurethane or silicone rubber, and then inserted, per arrow A, so that a central lumen 62 of each core member 60 defines that portion of the central lumen of assembly 210 which extends within each electrode E1-E8.

According to an exemplary embodiment, an inner diameter defined by inner surface 512 of each electrode E1-E8 can range from approximately 0.042 inch to approximately 0.044 inch, and an outer diameter of each core member 60 may be approximately 0.044 inch for a compression or line-to-line fit within the corresponding electrode E1-E8. According to some alternate methods, each core member 60 may be insert molded into the corresponding electrode E1-E8. It should be noted that a plurality of core members, each having a profile similar to either profile 40B or 40C of core member 40 may be incorporated in lieu of the plurality of core members 60, according to some additional alternate embodiments.

FIGS. 6A-B illustrate core member 60 including a plurality of channels arrayed around a circumference of central lumen 62, seven of which correspond to reference numeral 61, and one of which corresponds to reference numeral 61-EJ. Each channel 61, 61-EJ has an inward facing longitudinally extending opening 601, 601-EJ defined by adjacent ridges 64, 64-EJ, but only channel 61-EJ also has an outward facing longitudinally extending opening 611 communicating with electrode inner surface 512. According to the illustrated embodiment, each inward facing opening 601, 601-EJ provides access to press a length of one of conductors B1-B8 into the corresponding channel 61, 61E, and outward facing opening 611 of channel 61-EJ allows for the formation of an electrical junction 70, for example, as shown schematically in FIG. 7A. According to some preferred embodiments, ridges 64-EJ of each core member 60 apply an outward pressure, toward the corresponding inner surface 521, to force the corresponding swaged conductive sleeve 51 into intimate contact with inner surface 521 for subsequent welding that completes the formation of junction 70. According to an exemplary embodiment, inward facing opening 601-EJ of channel 61-EJ may have a width of about 0.009 inch.

FIG. 7A is an end view including a schematic representation of electrical junction 70, which is formed between second conductor B2 and inner surface 512 of second electrode E2, according to some embodiments. With reference back to FIG. 2A, second electrode E2 defines the proximal end of the length of electrode assembly 210. FIG. 7A illustrates electrical junction 70 being wedged within channel 61-EJ of one of the plurality of core members 60, and, similar to electrical junction 50 described above, a weld joint 72 of junction 70 may be formed by laser welding. Likewise, electrical junctions 70 may be formed between the other electrodes and the corresponding conductors of assembly 210, and wedged in channel 61-EJ of respective core members 60, for example, as indicated for electrodes E1, and E6-8 in FIG. 7B. FIG. 7B is a perspective view of a distal portion of electrode assembly 210, the distal end of the length thereof being defined by first electrode E1. FIG. 7B illustrates each conductive sleeve 51, which is swaged to the stripped cable at the distal end of the corresponding conductor conductors B1, B6-B8, wedged within each electrode core member 60 in proximity to the distal edge of the corresponding electrode E1, E6-8. As described above, a slight protrusion of each swaged sleeve 51 from the distal edge of the corresponding electrode E1-E8 can provide a visual guide for laser welding, wherein automated visualization can be employed to locate the protruding portion of each sleeve 51 and then position the laser source accordingly for a blind weld that penetrates through to inner surface 512 of each electrode E1-E8, to reach the corresponding conductive sleeve 51, and in some cases, through each conductive sleeve 51 as well, to reach filars F of the corresponding swaged conductor B1-B8.

According to the illustrated embodiment, lengths of conductors B1, B3-B8 that extend proximally from respective junctions 70 are held in respective channels 61 of electrode core members 60. Thus, FIG. 7A shows each conductor B1, B3-8 held within a corresponding channel 61 of core member 60 within electrode E2 at the proximal end of the length of electrode assembly 210 (FIG. 2A). According to an exemplary embodiment, and with reference back to FIG. 6B, each channel 61 has a circular profile with a diameter D that is greater than a width Y of opening 601 thereof, wherein diameter D may be about 0.007 inch, and width Y may be about 0.005 inch.

FIGS. 7A-B further illustrate electrical junctions 70 initially 'clocked' around central lumen 62 so that each conductor B1, B3-B8 extends in a relatively straight path. According to some methods, to provide some strain relief for conductors B1, B3-B8, each of electrodes B2-B8 may be rotated to a different degree about central lumen 62, so that the conductors extend along the helical path described above in conjunction with FIG. 3, prior to forming insulative spacers 2-8 (FIG. 2A). FIG. 7B illustrates an example of such a rotation of electrodes E6-E8, per arrows R6, R7, and R8. According to some embodiments, spacers 2-8 are formed by injecting an insulative material between adjacent electrodes, for example, as described above, wherein features of the mold may be configured to hold the rotated electrodes in place so that the helical path of conductors B1, B3-B8 is maintained while spacers 2-8 are formed. Also, as described above, distal-most tip 250 of lead 200 may be formed in the same injection molding process that forms spacers 2-8, according to some embodiments. According to some preferred embodiments, a durometer of the injected material is substantially the same as that of the material forming core members 60 to provide a smooth transition therebetween for conductors B1, B3-B8 when assembly 210 is subjected to bending. In an exemplary embodiment, each may be medical grade polyurethane having a 55 D durometer.

With further reference to FIGS. 7A-B, an elongate tubular sidewall 762 may extend along the length of assembly 210 to isolate channels 61, 61-EJ of core members 60 from central lumen 62, so that central lumen 62 may form an extension of the above described stylet lumen S (FIG. 2B). According to an exemplary embodiment, tubular sidewall 762 is formed from a medical grade fluoropolymer tube (e.g., polytetrafluoroethylene), along which electrodes E1-E8, with corresponding core members 60 and electrical junctions 70 are spaced and rotated, as described above, prior to the aforementioned molding process that forms spacers 2-8. According to an exemplary embodiment, tubular sidewall 762 has an inner diameter of approximately 0.018 inch, and an outer diameter of approximately 0.021 inch.

In the foregoing detailed description, the invention has been described with reference to specific embodiments. However, it may be appreciated that various modifications and changes can be made without departing from the scope of the invention as set forth in the appended claims; for example, in some alternative embodiments crimping may be employed in lieu of the above-described swaging.

The invention claimed is:

1. An electrode assembly for an implantable medical electrical lead, the assembly comprising:
   at least one core member formed from an insulating material, the at least one core member defining a central longitudinally extending lumen of the assembly, and each of the at least one core member including a plurality of longitudinally extending channels arrayed around a circumference of the central lumen, each channel having an opening that extends along an entire length thereof;
   a plurality of electrodes spaced apart from one another along a length of the assembly, a first electrode of the plurality defining a distal end of the length, and a second electrode of the plurality defining a proximal end of the length, the first electrode extending around the at least one core member;
   a plurality of elongate conductors corresponding to the plurality of electrodes, a first conductor of the plurality of conductors extending along a helical path, the helical path traveling from the proximal end of the length of the assembly to the distal end of the length of the assembly and around the central lumen of the assembly; and
   an electrical junction between the first conductor and an inner surface of the first electrode, the junction being wedged within a first channel of the plurality of channels of the at least one core member.

2. The assembly of claim 1, wherein the length thereof is between approximately 1 inch and approximately 3 inches, and the helical path travels approximately 360 degrees around the central lumen every 1 inch.

3. The assembly of claim 1, wherein the opening of each channel of the plurality of channels of the at least one core member faces outward, away from the central lumen.

4. The assembly of claim 1, wherein the electrical junction comprises a conductive sleeve swaged around a distal end of the first conductor, and a weld joint formed between the inner surface of the first electrode and the swaged conductive sleeve.

5. The assembly of claim 1, further comprising another, second electrical junction between a second conductor of the plurality of conductors and an inner surface of the second electrode, and wherein:
   the at least one core member comprises a single flexible core member extending along the length of the assembly;
   each channel of the plurality of channels of the single core member extends along a corresponding helical path that travels around the central lumen;
   the first conductor extends within the first channel along the length of the assembly;
   the second electrode extends around the single core member; and
   the second electrical junction is wedged within a second channel of the plurality of channels.

6. The assembly of claim 5, further comprising another, third electrical junction between a third conductor of the plurality of conductors and an inner surface of a third electrode of the plurality of electrodes, the third electrode extending around the core member, between the first electrode and the second electrode; and wherein:
   the third conductor extends within a third channel of the plurality of channels of the single core member, and along the helical path thereof; and
   the third electrical junction is wedged within the third channel.

7. The assembly of claim 6, wherein each electrical junction comprises a conductive sleeve swaged around a distal end of the corresponding conductor and a weld joint formed between the inner surface of the corresponding electrode and the corresponding swaged conductive sleeve.

8. The assembly of claim 5, wherein the central lumen defined by the single core member has a lubricious surface.

9. The assembly of claim 1, wherein:
   the at least one core member comprises a plurality of core members spaced apart from one another along the length of the assembly, a first core member of the plurality of core members including the first channel in which the electrical junction between the first conductor and the inner surface of the first electrode is wedged;
   each electrode of the plurality of electrodes extends around a corresponding core member; and
   the first conductor extends in a corresponding channel of each of the plurality of core members.

10. The assembly of claim 9, further comprising another, second electrical junction between a second conductor of the plurality of conductors and an inner surface of the second electrode, the second electrode extending around a second core member of the plurality of core members, and the second electrical junction being wedged within a channel of the second core member, the channel in which the second electrical junction is wedged being separate from the channel of the second core member in which the first conductor extends.

11. The assembly of claim 10, further comprising a third electrical junction between a third conductor of the plurality of conductors and an inner surface of a third electrode of the plurality of electrodes, the third electrode extending around a third core member of the plurality of core members and being located between the first electrode and the second electrode; and wherein:
   the third conductor extends within another channel of the second core member, the other channel being separate from the channel in which the first conductor extends and separate from the channel in which the second electrical junction is wedged; and
   the third electrical junction is wedged within a channel of the third core member, the channel in which the third electrical junction is wedged being separate from the channel of the third core member in which the first conductor extends.

12. The assembly of claim 11, wherein each electrical junction comprises a conductive sleeve swaged around a distal end of the corresponding conductor and a weld joint formed between the inner surface of the corresponding electrode and the corresponding swaged conductive sleeve.

13. The assembly of claim 9, wherein the opening of each channel of the plurality of channels of each core member faces inward toward the central lumen.

14. The assembly of claim 13, further comprising an elongate tubular sidewall extending along the length of the assembly to isolate the channels of the plurality of core members from the central lumen.

15. An implantable medical electrical lead comprising a connector, an electrode assembly, and an insulative body extending between the connector and the electrode assembly; and wherein the electrode assembly comprises:
   at least one core member formed from an insulating material, the at least one core member defining a central longitudinally extending lumen of the assembly, and each of the at least one core member including a plurality of longitudinally extending channels arrayed around a circumference of the central lumen, each channel having an opening that extends along an entire length thereof;
   a plurality of electrodes spaced apart from one another along a length of the assembly, a first electrode of the plurality defining a distal end of the length, and a second electrode of the plurality defining a proximal end of the length, the first electrode extending around the at least one core member;
   a plurality of elongate conductors corresponding to the plurality of electrodes, each conductor extending proximally from the electrode assembly, within the body, to the connector and being electrically coupled to the connector, a first conductor of the plurality of conductors extending along a helical path, the helical path traveling from the proximal end of the length of the assembly to the distal end of the length of the assembly and around the central lumen of the assembly; and
   an electrical junction between the first conductor and an inner surface of the first electrode, the junction being wedged within a first channel of the plurality of channels of the at least one core member.

16. The lead of claim 15, further comprising a distal-most tip located in close proximity to the distal end of the length of the electrode assembly; and wherein the electrode assembly further comprises a spacer located between adjacent electrodes of the plurality of electrodes, the distal-most tip of the lead and each spacer being integrally molded together from an insulative material.

17. The lead of claim 15, further comprising an elongate inner coil extending within the connector and the insulative body, and within the central lumen of the electrode assembly.

18. The lead of claim 15, wherein the length of the electrode assembly is between approximately 1 inch and approximately 3 inches, and the helical path of the assembly travels approximately 360 degrees around the central lumen every 1 inch.

19. The lead of claim 15, wherein the opening of each channel of the plurality of channels of the at least one core member of the electrode assembly faces outward, away from the central lumen.

20. The lead of claim 15, wherein the electrical junction of the electrode assembly comprises a conductive sleeve swaged around a distal end of the first conductor, and a weld joint formed between the inner surface of the first electrode and the swaged conductive sleeve.

21. The lead of claim 15, wherein the electrode assembly further comprises another, second electrical junction between a second conductor of the plurality of conductors and an inner surface of the second electrode, and wherein:
the at least one core member comprises a single flexible core member extending along the length of the assembly;
each channel of the plurality of channels of the single core member extends along a corresponding helical path that travels around the central lumen;
the first conductor extends within the first channel along the length of the assembly;
the second electrode extends around the single core member; and
the second electrical junction is wedged within a second channel of the plurality of channels.

22. The lead of claim 21, wherein the electrode assembly further comprises another, third electrical junction between a third conductor of the plurality of conductors and an inner surface of a third electrode of the plurality of electrodes, the third electrode extending around the core member, between the first electrode and the second electrode; and wherein:
the third conductor extends within a third channel of the plurality of channels of the single core member, and along the helical path thereof; and
the third electrical junction is wedged within the third channel.

23. The lead of claim 22, wherein each electrical junction of the electrode assembly comprises a conductive sleeve swaged around a distal end of the corresponding conductor and a weld joint formed between the inner surface of the corresponding electrode and the corresponding swaged conductive sleeve.

24. The lead of claim 21, wherein the central lumen defined by the single core member has a lubricious surface.

25. The lead of claim 15, wherein:
the at least one core member of the electrode assembly comprises a plurality of core members spaced apart from one another along the length of the assembly, a first core member of the plurality of core members including the first channel in which the electrical junction between the first conductor and the inner surface of the first electrode is wedged;
each electrode of the plurality of electrodes of the electrode assembly extends around a corresponding core member; and
the first conductor of the electrode assembly extends in a corresponding channel of each of the plurality of core members.

26. The lead of claim 25, wherein the electrode assembly further comprises another, second electrical junction between a second conductor of the plurality of conductors and an inner surface of the second electrode, the second electrode extending around a second core member of the plurality of core members, and the second electrical junction being wedged within a channel of the second core member, the channel in which the second electrical junction is wedged being separate from the channel of the second core member in which the first conductor extends.

27. The lead of claim 26, wherein the electrode assembly further comprises a third electrical junction between a third conductor of the plurality of conductors and an inner surface of a third electrode of the plurality of electrodes, the third electrode extending around a third core member of the plurality of core members and being located between the first electrode and the second electrode; and wherein:
the third conductor extends within another channel of the second core member, the other channel being separate from the channel in which the first conductor extends and separate from the channel in which the second electrical junction is wedged; and
the third electrical junction is wedged within a channel of the third core member, the channel in which the third electrical junction is wedged being separate from the channel of the third core member in which the first conductor extends.

28. The lead of claim 27, wherein each electrical junction of the electrode assembly comprises a conductive sleeve swaged around a distal end of the corresponding conductor and a weld joint formed between the inner surface of the corresponding electrode and the corresponding swaged conductive sleeve.

29. The lead of claim 25, wherein the opening of each channel of the plurality of channels of each core member of the electrode assembly faces inward toward the central lumen.

30. The lead of claim 29, wherein the electrode assembly further comprises an elongate tubular sidewall extending along the length of the assembly to isolate the channels of the plurality of core members from the central lumen.

31. An electrode component for an electrode assembly of an implantable medical electrical lead, the component comprising:
a core formed from an insulating material and defining a central longitudinally extending lumen of the component, the core including a plurality of longitudinally extending channels arrayed around the central lumen, each channel being sized to receive an elongate conductor therein, and each channel having an opening extending along an entire length thereof, each opening facing toward the central lumen; and
a longitudinally extending conductive layer overlaying the core; and
wherein a single channel of the plurality of channels of the core has another, second opening extending along the entire length thereof, the other opening facing toward an inner surface of the conductive layer.

32. The component of claim 31, wherein each channel of the core has a circular profile, except for the single channel that has the other, second opening facing toward the inner surface of the conductive layer, the circular profile having a diameter that is greater than a width of the opening of each channel.

33. The component of claim 31, wherein the other, second opening of the single channel has a width that is greater than the opening of the single channel that faces toward the central lumen.

34. A method for manufacturing an electrode assembly for a medical electrical lead, the electrode assembly comprising a plurality of electrodes spaced apart from one another along a length of the assembly, a first electrode of the plurality of electrodes defining a distal end of the length, and a second electrode of the plurality of electrodes defining a proximal end of the length, and the method comprising:

wedging a conductive distal end of a first conductor in a first channel within the first electrode so that the conductive distal end of the first conductor makes intimate contact with an inner surface of the first electrode, the first channel being formed by an insulative material inserted within the first electrode;

placing the first conductor in a second channel within the second electrode;

wedging a conductive distal end of a second conductor in a third channel within the second electrode so that the conductive distal end of the second conductor makes intimate contact with an inner surface of the second electrode, the third channel being formed by the insulative material inserted within the second electrode and being spaced apart from the second channel around a circumference of the central lumen;

electrically coupling the conductive wedged distal ends of the first and second conductors to the inner surface of the first and second electrodes, respectively; and injecting another insulative material between adjacent electrodes of the plurality of electrodes.

35. The method of claim 34, further comprising:

forming an elongate core from the insulative material, the core having a length greater than or equal to the length of the electrode assembly, the core including the first, second, and third channels, the first and second channels being contiguous and defining a helical path, which extends between the first and second electrodes, and along which the first conductor extends when placed in the second channel; and inserting the core within each electrode of the plurality of electrodes.

36. The method of claim 34 further comprising:

forming a plurality of cores from the insulative material, a first core of the plurality of cores including the first channel, and a second core of the plurality of cores including the second and third channels;

inserting each core of the plurality of cores into a corresponding electrode of the plurality of electrodes; and after inserting each core, clocking the first and second electrodes prior to placing the first conductor in the second channel within the second electrode.

* * * * *

UNITED STATES PATENT AND TRADEMARK OFFICE
CERTIFICATE OF CORRECTION

PATENT NO. : 10,449,353 B2  
APPLICATION NO. : 15/493932  
DATED : October 22, 2019  
INVENTOR(S) : Shoberg et al.

Page 1 of 1

It is certified that error appears in the above-identified patent and that said Letters Patent is hereby corrected as shown below:

On the Title Page

Item (72) should be corrected to read:  
Bret R. Shoberg, Hanover, MN (US);  
Gregory A. Boser, Richfield, MN (US);  
Michael T. Hegland, Mounds View, MN (US);  
Robert L. Olson, White Bear Lake, MN (US);  
Dale F. Seeley, Spring Park, MN (US);  
Jacob W. Silverberg, Blaine, MN (US);  
Suraj Rama, South Amboy, NJ (US);  
Jayesh R. Patel, Maple Grove, MN (US)

Signed and Sealed this  
Twenty-fifth Day of May, 2021

Drew Hirshfeld  
*Performing the Functions and Duties of the*  
*Under Secretary of Commerce for Intellectual Property and*  
*Director of the United States Patent and Trademark Office*